US00PP30107P3

(12) United States Plant Patent
Suphachadiwong

(10) Patent No.: US PP30,107 P3
(45) Date of Patent: Jan. 15, 2019

(54) ***VANDA* PLANT NAMED 'SPCDW1607'**

(50) Latin Name: ***Vanda* spp. Jones ex R. Br.**
Varietal Denomination: SPCDW1607

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,166

(22) Filed: Sep. 27, 2017

(65) Prior Publication Data

US 2018/0092274 P1 Mar. 29, 2018

(30) Foreign Application Priority Data

Sep. 27, 2016 (QZ) ..... PBR 2016/2334

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Vanda* plant named 'SPCDW1607' which is characterized by vigorous growth, a large plant size with relatively large flowers, inflorescence with a large quantity of open flowers, vibrant yellow flowers that are finely to moderately dotted greyed-orange, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1607'.

CROSS REFERENCE TO RELATED APPLICATIONS

This application claims priority to the Community Plant Variety Rights application number 2016/2334, filed Sep. 27, 2016, which is herein incorporated by reference.

BACKGROUND OF THE INVENTION

Parentage: The *Vanda* variety 'SPCDW1607' is the result of a planned breeding program. The new variety originated as a seedling from the crossing of *Vanda* 'CTHA' (not patented), the seed parent, with *Vanda* 'AL69' (not patented), the pollen parent. Both parents were developed by, and are owned by, the inventor and were never commercially released. The crossing was made by the inventor in his research greenhouse in Bangphra, Thailand in August of 1994.

The new variety was first selected in February of 1999, in a research greenhouse in Bangphra, Thailand belonging to the inventor. After identifying the new variety as a potentially interesting selection, the inventor continued confidential testing and propagation of 'SPCDW1607', assessing stability of the unique characteristics of this variety.

Asexual Reproduction: Asexual reproduction of the new cultivar 'SPCDW1607', by way of mericloning, was first initiated in October of 2008 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1607' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1607'. These characteristics in combination distinguish 'SPCDW1607' as a new and distinct *Vanda* cultivar:

1. *Vanda* 'SPCDW1607' is a vigorous plant which exhibits a large plant size with large flowers; and
2. *Vanda* 'SPCDW1607' exhibits an inflorescence with a relatively large quantity of open flowers; and
3. *Vanda* 'SPCDW1607' exhibits vibrant yellow petals and sepals, all of which are dotted greyed-orange; and
4. *Vanda* 'SPCDW1607' exhibits lateral petals and a dorsal sepal which are all finely dotted greyed-orange; and
5. *Vanda* 'SPCDW1607' exhibits lateral sepals which are densely dotted greyed-orange; and
6. *Vanda* 'SPCDW1607' exhibits a labellum with a yellow-green central lobe that is striped greyed-orange, and green-yellow coloured lateral lobes.

BOTANICAL DESCRIPTION OF THE PLANT

Figure 1:
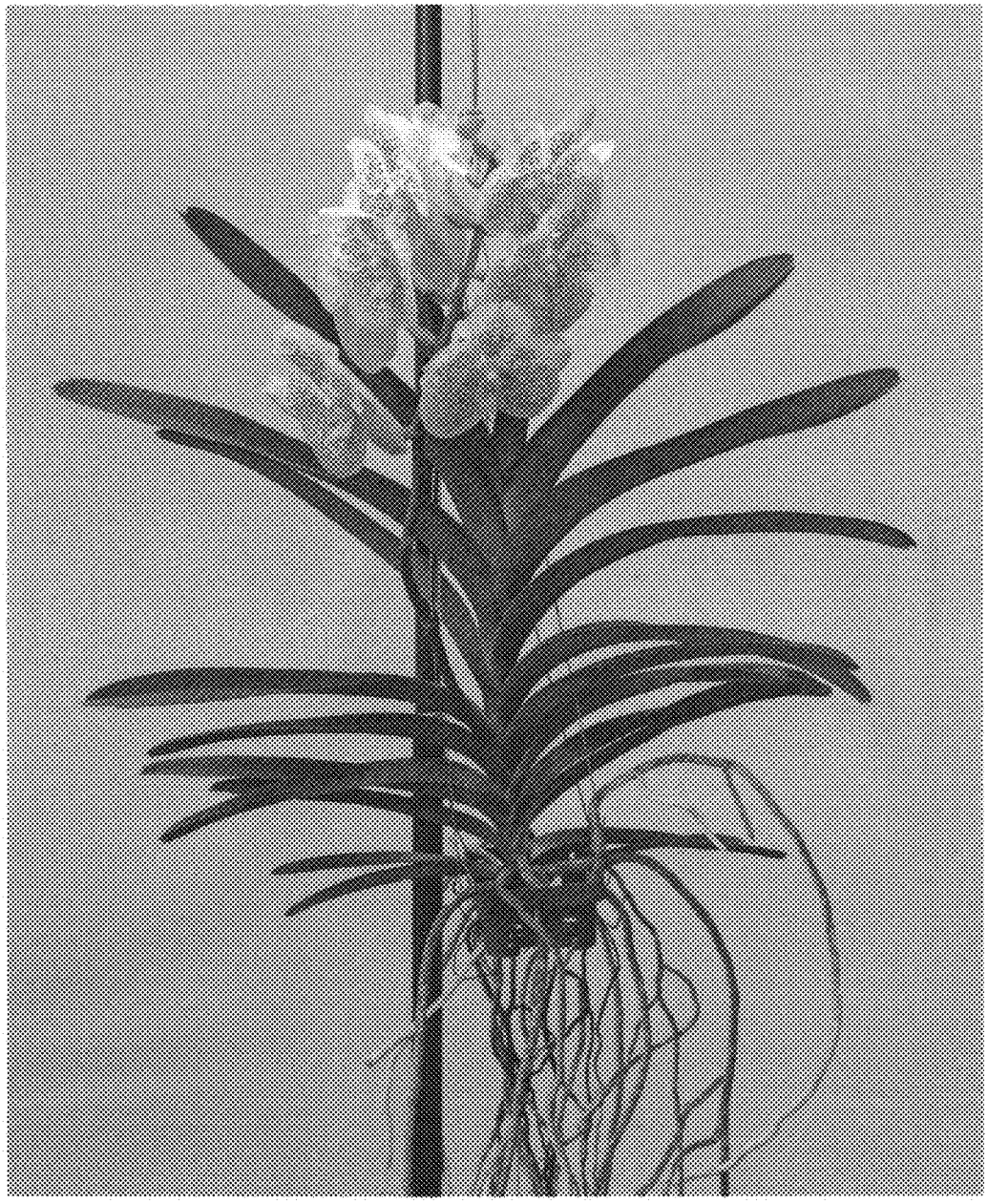
FIG. 1 illustrates, as nearly true as it is reasonably possible to make the same in color photographs of this type, an exemplary plant of 'SPCDW1607' grown in a commercial greenhouse in Honselersdijk, the Netherlands. This plant is approximately 6 years old from the time of mericloning, shown planted in an 8 by 8 cm container.
Figure 2:
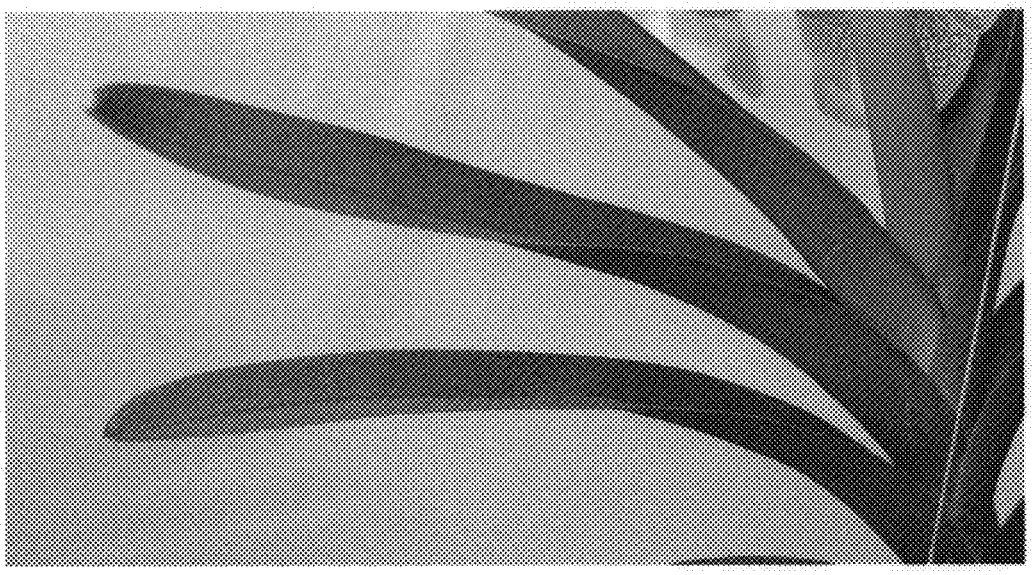
FIG. 2 illustrates, as nearly true as it is reasonably possible to make the same in color photographs of this type, the typical foliage of 'SPCDW1607'.
Figure 3:
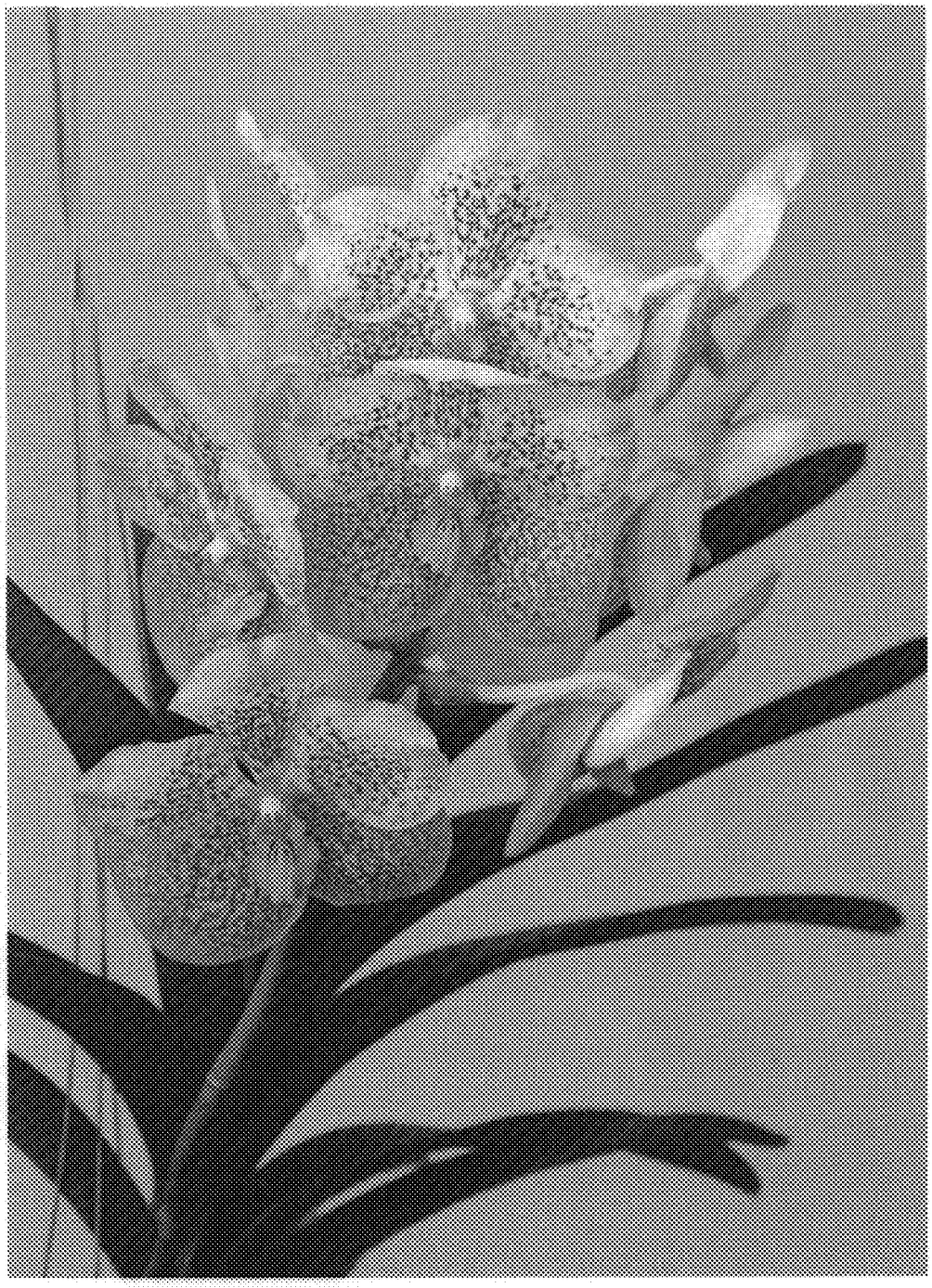
FIG. 3 illustrates, as nearly true as it is reasonably possible to make the same in color photographs of this type, the typical inflorescence of 'SPCDW1607'.
Figure 4:
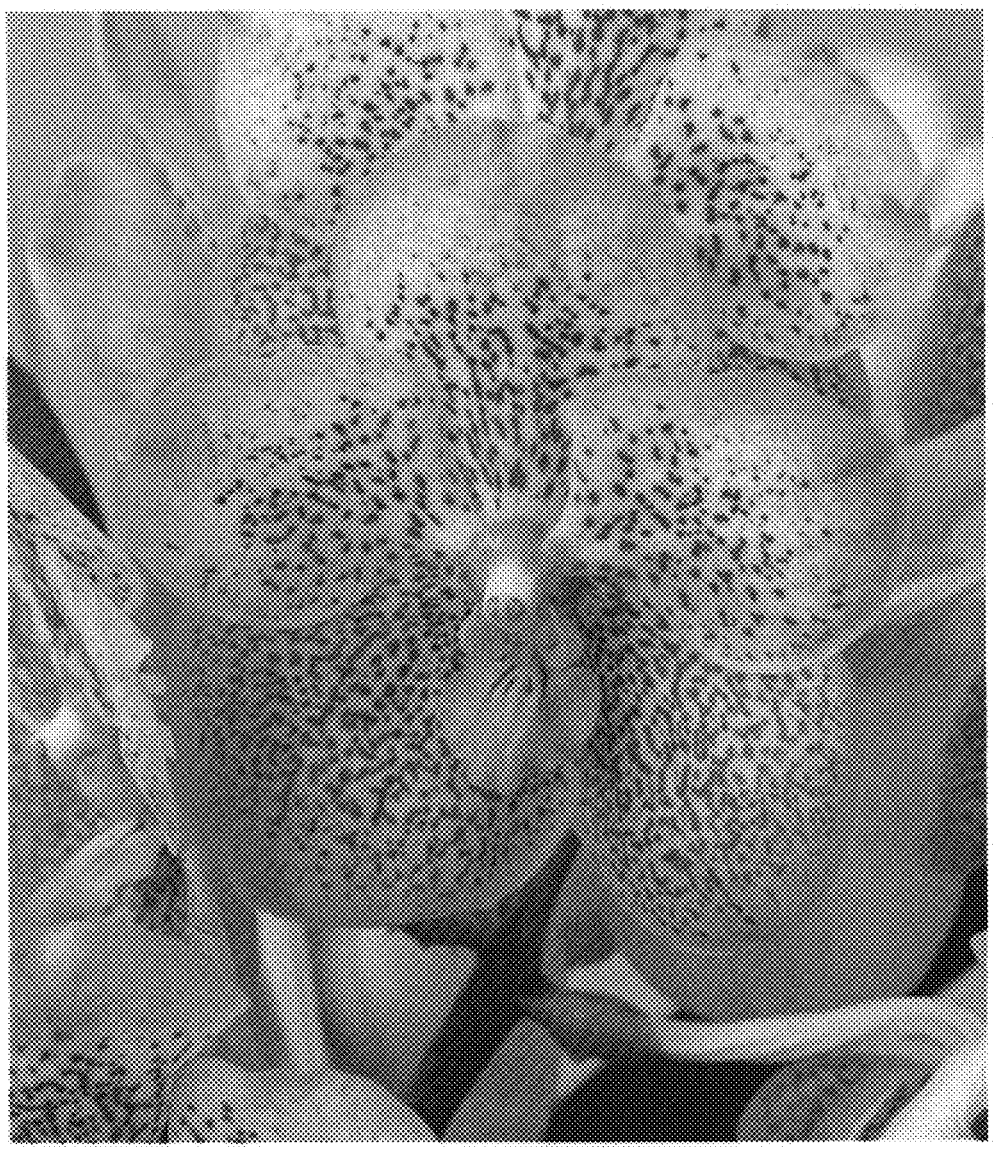
FIG. 4 illustrates, as nearly true as it is reasonably possible to make the same in color photographs of this type, the typical flower of 'SPCDW1607'.

The following observations and measurements made in September of 2017 describe averages from a sample set of six specimens of six year-old 'SPCDW1607' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1607' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1607' and comparisons with the parents and most similar commercial variety of *Vanda* are provided below.

Plant description:

- *Growth habit*.—Perennial; monopodial, upright. Single monopodial leafy stem, with flowers carried level with or slightly above the leaf plane; inflorescences growing from the leaf axils.
- *Average height from base (plant grown in hanging basket, so no soil line present) to foliar plane*.—47.3 cm.
- *Average height from base (plant grown in hanging basket, so no soil line present) to top of floral plane*.—49.5 cm.
- *Plant spread*.—Average of 50.0 cm.
- *Appropriate container size*.—8 cm by 8 cm rectangular hanging basket.
- *Growth rate*.—Moderate.
- *Plant vigor*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Plants have not been observed to be susceptible or resistant to pathogens and pests common to *Vanda*.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Moderately dense rooting; with aerial roots only.
- *Dimensions, mature roots*.—70.0 cm long with a diameter of 0.4 cm, on average.
- *Texture*.—Very fleshy; non-fibrous.
- *Color*.—Greyed-green, nearest to RHS 192D; root apex is yellow-green, RHS 146A.

Stem:

- *Branching habit*.—Monopodial; no lateral branches present.
- *Number of primary (main) stems per plant*.—One.
- *Number of secondary (lateral) branches per plant*.—None.
- *Appearance and shape*.—Circular, formed by the leaf sheaths.
- *Length*.—25.4 cm.
- *Diameter*.—1.2 cm.
- *Internode length*.—1.2 cm.
- *Luster*.—Matte.
- *Aspect, main stem*.—Near vertical.
- *Strength*.—Very strong.
- *Color, juvenile*.—Yellow-green, nearest to in between RHS 150C and 150D.
- *Color, mature*.—Yellow-green, nearest to RHS 150C.
- *Color at internodes*.—Yellow-green, nearest to RHS 150C.
- *Pubescence*.—Glabrous.

Foliage:

- *Arrangement*.—Distichous.
- *Dimensions*.—28.1 cm long, excluding the sheath, and 3.4 cm wide.
- *Shape of blade*.—Ligulate; moderately to strongly carinate.
- *Aspect*.—Slightly curved.
- *Apex*.—Unequal praemorse.
- *Base*.—Sheathing.
- *Sheath dimensions*.—3.9 cm long and 2.0 cm wide, on average.
- *Sheath color*.—Yellow-green, nearest to in between RHS N144B and 145A.
- *Margin*.—Entire.
- *Pubescence, texture and luster of adaxial surface*.—Glabrous, smooth, and matte.
- *Pubescence, texture and luster of abaxial surface*.—Glabrous, smooth, and matte.
- *Color*.—Juvenile foliage, adaxial surface — Yellow-green, nearest to RHS 144B, and fading to green towards the margins, nearest to RHS 137A. Juvenile foliage, abaxial surface — Yellow-green, nearest to RHS 144B, and fading to green towards the margins, nearest to RHS 137B. Mature foliage, adaxial surface — Nearest to a combination of yellow-green, RHS 147A, and greyed-green, nearest to RHS N189A but slightly darker. Mature foliage, abaxial surface — Nearest to in between green, RHS 137B, and yellow-green, RHS 147B.

*Venation*.—Parallel.

*Venation color, adaxial surface*.—Nearest to a combination of yellow-green, RHS 147A, and greyed-green, nearest to RHS N189A but slightly darker.

*Venation color, abaxial surface*.—Green, RHS 143A.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 13.

*Flowers per plant*.—11 open flowers and 2 flower buds.

*Inflorescence height*.—Approximately 22.0 cm (measured from base of lowest flower to top of upper flower).

*Inflorescence diameter*.—Approximately 17.2 cm.

*Peduncle*.—Dimensions — Approximately 34.0 cm long and 0.6 cm wide. Aspect — Generally at a 30 degree angle to lateral branch axis. Strength — Moderately strong. Texture and luster — Glabrous and slightly glossy. Color — Green, nearest to RHS 143A.

Bud:

*Length*.—Average of 1.4 cm.

*Diameter*.—Average horizontal diameter is 1.6 cm; the vertical diameter is 1.8 cm.

*Shape*.—Cubic to globular, with a deltoid apex which is pointed downward.

*Pubescence, texture and luster*.—Glabrous, smooth and matte.

*Color*.—Yellow-green, nearest to a combination of RHS 151B and 151C, and darker towards the apex, nearest to RHS 151A.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals slightly to moderately overlap the lateral sepals and slightly overlap the dorsal sepal; lateral sepals moderately overlap one another.

*Aspect*.—Flowers are outward-facing to slightly nodding.

*Vertical height*.—Approximately 9.8 cm.

*Diameter*.—Approximately 8.7 cm.

*Depth*.—Approximately 2.8 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.4 cm. Width — Approximately 3.9 cm. Shape — Broad obovate. Apex — Obtuse to very bluntly acute. Base — Cuneate. Margin — Entire; not undulated to slightly undulated. Pubescence, texture and luster of upper surface — Glabrous, velvety and matte. Pubescence, texture and luster of lower surface — Glabrous, velvety and matte. Color when opening, upper surface — Yellow, nearest to RHS 2D, darker towards the apex, nearest to RHS 3C, fading to yellow-green towards the base, nearest to RHS 154D; finely dotted greyed-orange, nearest to RHS N167A; dots at the base of the petal are a lighter shade of greyed-orange, nearest to RHS 167D. Color when opening, lower surface — Yellow, nearest to RHS 2D, and fading darker towards the apex, nearest to RHS 3C; finely dotted greyed-white, nearest to RHS 156A. Color when fully opened, upper surface — Yellow, nearest to RHS 3D, and fading to a combination of yellow, nearest to RHS 11B, and greyed-yellow, nearest to a combination of RHS 160A and 160B, towards the apex; fading to yellow-green towards the base, nearest to a combination of RHS 154B and 154C; base is yellow-green, RHS 150B; petal is finely dotted greyed-orange, nearest to RHS N166B. Color when fully opened, lower surface — Yellow, nearest to RHS 2D, and fading to a combination of darker yellow, nearest to RHS 11B, and greyed-yellow, nearest to RHS 161B, towards the apex; finely dotted greyed-white, nearest to RHS 156B. Fading, upper surface — Not fading. Fading, lower surface — Not fading. Venation — Densely reticulate. Venation color, fully opened, upper surface — Yellow, nearest to RHS 3D, and fading to a combination of yellow, nearest to RHS 11B, and greyed-yellow, nearest to a combination of RHS 160A and 160B, towards the apex; fading to yellow-green towards the base, nearest to a combination of RHS 154B and 154C. Venation color, fully opened, lower surface — Yellow, nearest to RHS 2D, and fading to a combination of darker yellow, nearest to RHS 11B, and greyed-yellow, nearest to RHS 161B.

*Labellum*.—Shape — Three-lobed; the shape of the lateral lobes is obovate, and the aspect is concave; the shape of the central lobe is ovate, and the aspect is slightly convex. Length — Central lobe — Approximately 2.0 cm. Lateral lobes — Approximately 0.9 cm. Width — Central lobe — Approximately 1.7 cm; 1.3 at the apex. Lateral lobes — Approximately 0.7 cm. Apex — Central lobe — Emarginate. Lateral lobes — Obtuse. Base — Central lobe — Cuneate. Lateral lobes — Cuneate. Margin — Central lobe — Entire; moderately undulated. Lateral lobes — Entire; not undulate. Texture and luster of upper surface — Central lobe — Glabrous, velvety, and matte with the exception of the apex which is glossy. Lateral lobes — Glabrous, velvety, and matte. Texture and luster of lower surface — Central lobe — Glabrous, velvety, and matte with the exception of the apex which is glossy. Lateral lobes — Glabrous, velvety, and matte. Color when opening, upper surface — Central lobe — Yellow-green, nearest the RHS N144A, and fading lighter towards the base, nearest to RHS 145C; spaces in between callosities are striped greyed-orange, nearest to RHS 165A. Lateral lobes — Green-yellow, nearest the RHS 1C; base is suffused with yellow, RHS 13A. Color when opening, lower surface — Central lobe — Yellow-green, nearest to in between RHS N144A and 151B, and fading lighter towards the base, nearest to RHS 145C. Lateral lobes — Green-yellow, nearest the RHS 1C. Color when fully opened, upper surface — Central lobe — Yellow-green, nearest the RHS N144A, and fading lighter towards the base, nearest to RHS 145C; spaces in between callosities are striped greyed-orange, nearest to RHS 165A. Lateral lobes — Yellow-green, nearest the RHS 150D, and fading lighter towards the apex, nearest to a combination of RHS 145A and 145B; base is suffused with yellow, RHS 13A. Color when fully opened, lower surface — Central lobe — Yellow-green, nearest to in between RHS N144A and 151B, and fading lighter towards the base, nearest to RHS 145C. Lateral lobes — Yellow-green, nearest the RHS 150D, and darker towards the apex, nearest to RHS 149C. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.6 cm long and 0.6 cm wide, on average. Color — Yellow-green, nearest to RHS N144A, and fading lighter towards the base, nearest to RHS 145C.

*Spurs*.—Quantity — Average of 1. Length — Approximately 0.3 cm. Diameter — Approximately 0.2 cm. Vertical height — Approximately 0.4 cm, at the base. Shape — Short triangular; flattened. Apex — Bluntly acute. Base — Broad cuneate. Pubescence, texture and luster — Glabrous, smooth, and matte. Color — Yellow-green, nearest to RHS 150D; distal half is darker, nearest to RHS 150C.

*Sepals*.—Quantity — Average of 3 unfused sepals. Arrangement — One dorsal sepal and two lateral sepals. Length — Dorsal sepal — Approximately 5.0 cm. Lateral sepals — Approximately 4.9 cm. Width — Dorsal sepal — Approximately 4.2 cm. Lateral sepals — Approximately 5.3 cm. Shape — Dorsal sepal — Broad ovate. Lateral sepals — Reniform. Apex — Dorsal sepal — Rounded. Lateral sepals — Rounded. Base — Dorsal sepal — Cuneate. Lateral sepals — Cuneate. Margin — Dorsal sepal — Entire; not undulated. Lateral sepals — Entire; not undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Yellow, nearest to RHS 2D, darker towards the apex, nearest to RHS 3C, fading to yellow-green towards the base, nearest to RHS 154D; sepal is finely dotted greyed-orange, nearest to RHS N167A; dots at the base of the sepal are a lighter shade of greyed-orange, nearest to RHS 167D. Lateral sepals — Yellow-green, nearest to RHS 151B, and darker towards the apex, nearest to RHS 151A; suffused with green towards the base, nearest to RHS 150B; sepal is densely dotted greyed-orange, nearest to RHS 166C. Color when opening, lower surface — Dorsal sepal — Yellow, nearest to RHS 2D, and darker towards the apex, nearest to RHS 3C, with a dark central blotch, nearest to RHS 11A; sepal is finely dotted greyed-white, nearest to RHS 156A. Lateral sepals — Yellow-green, nearest to RHS 154D, and darker towards the apex, nearest to RHS 151A; suffused with green towards the base, nearest to RHS 150B; sepal is densely dotted with small greyed-white dots, nearest to RHS 156A. Color when fully opened, upper surface — Dorsal sepal — Yellow, nearest to RHS 3D, and fading to a combination of yellow, nearest to RHS 11B, and greyed-yellow, nearest to RHS 160A, towards the apex; fading to yellow-green towards the base, nearest to a combination of RHS 154B and 154C; base is yellow-green, RHS 150B; sepal is finely dotted greyed-orange, nearest to RHS 166B. Lateral sepals — Yellow-green, nearest to RHS 151B, and darker towards the apex, nearest to RHS 151A; suffused with green towards the base, nearest to RHS 150B; sepal is densely dotted with small greyed-orange dots, nearest to RHS 166C. Color when fully opened, lower surface — Dorsal sepal — Yellow, nearest to RHS 2D, and fading to a combination of darker yellow, nearest to RHS 11B, and greyed-yellow, nearest to RHS 160A, towards the apex; finely dotted greyed-white, nearest to RHS 156B. Lateral sepals — Yellow-green, nearest to RHS 154D, and darker towards the apex, nearest to RHS 151A; sepal is densely dotted with small greyed-white dots, nearest to RHS 156A. Fading, upper surface — Not fading. Fading, lower surface — Not fading. Venation — Densely reticulate. Venation color, fully opened, upper surface — Dorsal sepal — Yellow, nearest to RHS 3D, and fading to a combination of yellow, nearest to RHS 11B, and greyed-yellow, nearest to RHS 160A, towards the apex; fading to yellow-green towards the base, nearest to a combination of RHS 154B and 154C. Lateral sepals — Yellow-green, nearest to RHS 151B, and darker towards the apex, nearest to RHS 151A; suffused with green towards the base, nearest to RHS 150B. Venation color, fully opened, lower surface — Dorsal sepal — Yellow, nearest to RHS 2D, and fading to a combination of darker yellow, nearest to RHS 11B, and greyed-yellow, nearest to RHS 160A. Lateral sepals — Yellow-green, nearest to RHS 154D, and darker towards the apex, nearest to RHS 151A.

*Pedicels*.—Length — Approximately 5.4 cm. Diameter — Approximately 0.4 cm. Angle — Approximately 70 degree angle to peduncle axis. Strength — Moderate. Texture — Glabrous, axially angled with 5 "ribs", axially twisted (due to resupination). Luster — Glossy. Color — Yellow-green, nearest to RHS 145A, and fading lighter towards the distal end, nearest to RHS 145D.

*Bract*.—Quantity — One bract present at the base of each pedicel. Shape — Broad obovate; folded around the base of each pedicel. Dimensions — Average of 1.8 cm long and 1.5 cm wide. Apex — Obtuse. Base — Broad cuneate. Margins — Entire. Color, inner surface — Yellow-green, nearest to RHS 144B. Color, outer surface — Yellow-green, nearest to RHS 144A.

Reproductive organs:

*Column*.—Length — Approximately 0.6 cm. Diameter — Approximately 0.5 cm. Color — Yellow-green, nearest to in between RHS 151D and 154B.

*Ovary*.—Position — Inferior. Diameter — Approximately 0.4 cm. Color — Yellow-green, nearest to RHS 145A.

*Pollinia color*.—Yellow-orange, nearest to RHS 17C.

Seed and fruit: No fruit and seed production has been detected to date.

Comparison With the Parent Plants

Plants of the new cultivar 'SPCDW1607' differ from the *Vanda* seed parent, 'CTHA' (not patented), by the characteristics described in Table 1.

TABLE 1

| Characteristic | 'SPCDW1607' | 'CTHA' |
|---|---|---|
| Number of open flowers on the inflorescence. | More than 'CTHA'. | Less than 'SPCDW1607'. |
| Flower size. | Larger than 'CTHA'. | Smaller than 'SPCDW1607'. |
| General coloration of the petals and sepals (excluding the overlaid color pattern) when fully opened. | Vibrant yellow. | Greyed-yellow. |

Plants of the new cultivar 'SPCDW1607' differ from the *Vanda* pollen parent, *Vanda* 'AL69' (not patented), by the characteristics described in Table 2.

TABLE 2

| Characteristic | 'SPCDW1607' | 'AL69' |
|---|---|---|
| Plant vigor. | More vigorous than 'AL69'. | Less vigorous than 'SPCDW1607'. |
| Plant size. | Larger than 'AL69'. | Smaller than 'SPCDW1607'. |
| Flower size. | Larger than 'AL69'. | Smaller than 'SPCDW1607'. |

TABLE 2-continued

| Characteristic | 'SPCDW1607' | 'AL69' |
|---|---|---|
| General coloration of the petal and sepal color, and the overlaid color pattern, when fully opened. | Vibrant yellow with greyed-orange dotting. | Yellow and white bicolor, without any overlaid color pattern. |

Comparison With the Most Similar *Vanda* Cultivar Known to the Inventor

Plants of the new cultivar 'SPCDW1607' are most similar to the cultivar, *Vanda* 'SPCDW1514' (U.S. Pat. No. 29,307). A comparison of 'SPCDW1607' with *Vanda* 'SPCDW1514' is described in Table 3.

TABLE 3

| Characteristic | 'SPCDW1607' | 'SPCDW1514' |
|---|---|---|
| General coloration of the petals and sepals (excluding the overlaid color pattern) when fully opened. | Vibrant yellow. | Greyed-yellow. |
| Color pattern on the petals and sepals. | Finely dotted greyed-orange. | Densely dotted greyed-purple. |
| General coloration of the central lobe of the labellum. | Yellow with long, narrow greyed-orange stripes between callosities. | Yellow with prominent greyed-orange blotches between callosities and greyed-orange suffusion across the central lobe. |

That which is claimed is:

1. A new and distinct variety of *Vanda* plant named 'SPCDW1607', substantially as described and illustrated herein.

* * * * *